United States Patent [19]

Schubert et al.

[11] Patent Number: 5,678,539
[45] Date of Patent: Oct. 21, 1997

[54] RESPIRATOR WITH AN INPUT AND OUTPUT UNIT

[75] Inventors: Ernst-Wilhelm Schubert; Roland Zarske, both of Lübeck, Germany; Hans Wagner, Vienna, Austria

[73] Assignee: Drägerwerk Aktiengesellschaft, Lübeck, Germany

[21] Appl. No.: 574,273

[22] Filed: Dec. 18, 1995

[30] Foreign Application Priority Data

Jan. 11, 1995 [DE] Germany .......... 195 00 529.5

[51] Int. Cl.⁶ .................................................. A61M 16/00
[52] U.S. Cl. ............................ 128/204.21; 128/205.23
[58] Field of Search .................... 128/204.21, 204.23, 128/204.18, 200.24, 205.11, 205.23, 203.12, DIG. 13; 364/413.03

[56] References Cited

U.S. PATENT DOCUMENTS

| | | | |
|---|---|---|---|
| 4,957,107 | 9/1990 | Sipin | 128/204.21 |
| 5,007,429 | 4/1991 | Treatch et al. | 128/677 |
| 5,107,831 | 4/1992 | Halpern et al. | 128/204.26 |
| 5,231,981 | 8/1993 | Schreiber et al. | 128/205.23 |
| 5,237,987 | 8/1993 | Anderson et al. | 128/204.18 |
| 5,429,123 | 7/1995 | Shaffer et al. | 128/204.23 |
| 5,442,940 | 8/1995 | Secker et al. | 128/670 |
| 5,464,392 | 11/1995 | Epstein et al. | 604/67 |

FOREIGN PATENT DOCUMENTS 39 23 568 C1  6/1990  Germany .

*Primary Examiner*—Kimberly L. Asher
*Assistant Examiner*—Eric P. Raciti
*Attorney, Agent, or Firm*—McGlew and Tuttle

[57] ABSTRACT

A respirator is provided with a gas-metering device for respiration gases, a control unit influencing and monitoring the metering of the gas, an input unit connected to the control unit for introducing commands into the control unit, a display unit outputting parameters, a rotary knob changing preselected parameters, and with an acknowledge switch, which takes over the changed parameter as a new set value into the control unit and is actuated by the rotary knob. The display unit is designed as an interactive flat screen with a contact-sensitive surface. Data entry sectors with setting segments and output sectors for parameters to be displayed are provided within the flat screen. The input unit is designed as a keypad arranged on the side of the flat screen. At least preselected data entry sectors on the flat screen can be switched by means of the keypad. The rotary knob and/or the acknowledge switch are/is switched into functional connection with the selected setting segment by touching at least one of the setting segments within a data entry sector.

11 Claims, 2 Drawing Sheets

RESPIRATOR WITH AN INPUT AND OUTPUT UNIT

FIELD OF THE INVENTION

The present invention pertains to a respirator with a gas-metering device for respiration gases, a control unit influencing and monitoring the metering of the gas, an input unit connected to the control unit for introducing commands into the control unit, a display unit outputting control parameters and measured parameters, an input element changing preselected parameters, and an acknowledge switch which takes over the changed parameter as a new set value into the control unit.

BACKGROUND OF THE INVENTION

A respirator with a mixing and metering device for medical gases for supplying oxygen/breathing gas for a patient has become known from U.S. Pat. No. 5,237,987. The prior-art respirator has a control unit, with which the respiration parameters are set and monitored according to the user's preset values. The set values to be set and monitored are provided for the user within menu structures via a display unit.

Should respiration parameters be changed, the user can first select the parameter to be changed within the menu structure by means of a centrally arranged rotary knob, select the parameter to be changed by pressing an acknowledge switch, then change the value of the selected parameter with the rotary knob, and take over the newly set parameter as a new set value for the respirator into the control unit by pressing the acknowledge switch. It is possible to switch over between a menu structure which displays the respiration parameters and a menu structure which changes the respiration parameters by means of an input switch arranged next to the display unit.

The disadvantage of the prior-art respirator is the fact that parameters to be set must first be selected by means of a rotary knob to be then able to be changed. This makes the operation of the respirator difficult in routine clinical practice, because a direct access to the parameter to be changed is frequently necessary.

An operating and information unit for a protective suit has become known from DE 39 23 568 C1. The prior-art device comprises a swing-out LCD screen with a contact-sensitive surface, which is divided into five different sectors. Three of the five sectors on the LCD screen are used as data entry surfaces for entering parameters, and the other two sectors are intended for the display of certain parameters. One of the three data entry sectors is designed as a selector switch between different sets of information. When this data entry sector is depressed, the display of the information just selected appears in a display sector, and a characteristic parameter, which is to be changed, appears in another display sector. The change is performed via the remaining two data entry sectors, using, e.g., one data entry sector for increasing the parameter and another data entry sector for decreasing the parameter.

The disadvantage of the prior-art operating unit is the fact that a parameter to be changed must first be selected from a menu complex, and a direct access to this parameter is not possible.

SUMMARY AND OBJECTS OF THE INVENTION

The primary object of the present invention is to improve a respirator of the type described above such that setting parameters can be displayed in a clear form and can be changed by the user in a simple manner.

This object is attained by the display unit being designed as an interactive flat screen with a contact-sensitive surface; by data entry sectors with setting segments and output sectors for parameters to be displayed being provided within the flat screen; by the input unit being designed as a keypad; by at least preselected data entry sectors being switchable on the flat screen by means of the keypad; and by the input element and/or the acknowledge switch being switched into functional connection with the preselected setting segment by touching at least one of the setting segments within one of the data entry sectors.

The advantage of the present invention is essentially the fact that the setting of parameters, e.g., respiration parameters, or the selection of forms of respiration are performed via data entry sectors of a contact-sensitive flat screen (touch screen), and that the parameters to be changed are switched into functional connection with the input element by touching the setting segment and the value of the parameter can then be changed by means of the input element if this element is intended for the parameter. By actuating the acknowledge switch, which is also switched into functional connection with the input element on being touched, an acknowledge function is activated, and the newly set respiration parameter is taken over as a new set value into the control unit. In the simplest case, the input element is a rotary knob, with which the changing of the value of the parameter is performed, and the acknowledge switch is connected to the rotary knob such that the acknowledge function is triggered by depressing the rotary knob. However, it is also possible to design the input element by means of two discrete keys, in which case the parameter is increased with one of the keys and decreased with the other. If changing the value of the parameter is intended, the selected parameter is taken over as a new set value by actuating the acknowledge switch.

The form of respiration-setting segments, with which a defined form of respiration can be selected, are advantageously provided within individual data entry sectors, and there are parameter-setting segments, with which the patient-related respiration parameters, e.g., the oxygen concentration ($O_2$), the respiration gas flow (V), the inspiration time ($T_i$), the respiration rate (f), the stroke volume ($V_t$), the maximum pressure ($P_{max}$), and the PEEP pressure, can be set. Only the respiration parameter-setting segments within the data entry sector which are relevant for the selected form of respiration are displayed.

The respiration parameter-setting segments are advantageously represented as adjusting knobs on the flat screen to visually illustrate to the user that the respiration parameters can be continuously changed.

The form Of respiration-setting segments are advantageously represented as push-buttons on the flat screen. By touching one of the form of respiration-setting segments, corresponding forms of respiration (IPPV, BIPAP, CPAP) can be directly selected, and they can be taken over as a new set value by actuating the acknowledge switch.

The set value of the parameter is advantageously displayed within the form of respiration-setting segments, The keypad is advantageously arranged outside the flat screen, preferably on the side, next to the flat screen.

The flat screen, the keypad and the input element with the acknowledge switch are advantageously designed as an operating unit which is pivotable in relation to the respirator. The flat screen can thus be pivoted into a position favorable for the user in order to achieve easy readability, but also to eliminate interfering light reflexes.

The operating unit is advantageously designed as a component removable from the respirator, so that it can be fastened on any desired side of the respirator, but also in another, ergonomically more favorable area, detached from the respirator. To do so, the operating unit is provided with a fastening claw, which makes it possible to arrange the operating unit on a wall rail.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
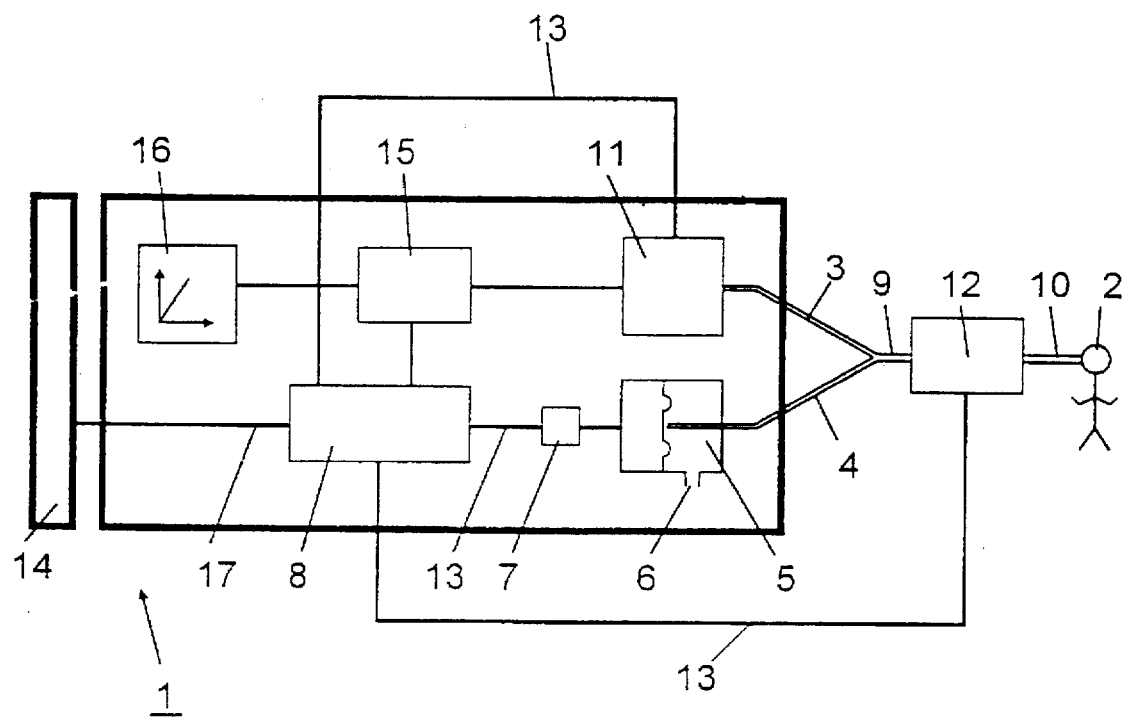
FIG. 1 is a schematic view of a respirator with a detachable operating unit.

FIG. 1 shows a respirator 1 for supplying a patient 2 with respiration gas via an inspiration line 3 and for removing the expired gas via an expiration line 4 and an expiration valve 5 to an expiration outlet 6. The expiration valve 5, which sets a pressure at the patient during the inspiration and the expiration, is actuated by a control valve 7, which is connected to a control unit 8 of the respirator via a signal line 13. The inspiration line 3 and the expiration line 4 unite in a Y-piece 9, from which a respiration gas line 10 which is common for the inspiration and the expiration leads to the patient 2. A respiration pressure sensor 11 for measuring the respiration gas pressure p is arranged in the inspiration line 3, and a respiration gas flow sensor 12 for measuring the respiration gas flow V is arranged in the respiration gas line 10, and the sensors 11, 12 are connected to the control unit 8 via signal lines 13. Here, the respiration gas flow V is the time derivative of the respiration gas volume per unit of time. The respiration gas flow V to the patient 2 is metered via respiration flow control valves 15, which are connected to pressurized gas sources, not shown in FIG. 1, and receive preset values for the respiration from a ramp generator 16 during the inspiration. The respiration flow control valves 15 are illustrated as a block in FIG. 1. The input of the respiration parameters and the output of measured curves and measured values, which are to illustrate the course of the respiration over time, are performed via a central operating unit 14, which is removable from the respirator 1 and is connected to the control unit 8 via a line 17. The control unit 8 contains a microprocessor unit, not shown in FIG. 1, which controls the respiration functions according to the respiration parameters entered via the operating unit 14 and evaluates the measured signals sent by the sensors 11, 12. The control unit 8 also contains a memory, in which suggested values for respiration parameters are stored and can be polled via the operating unit 14. The suggested values are derived from the body weight of the patient 2.

Figure 2:
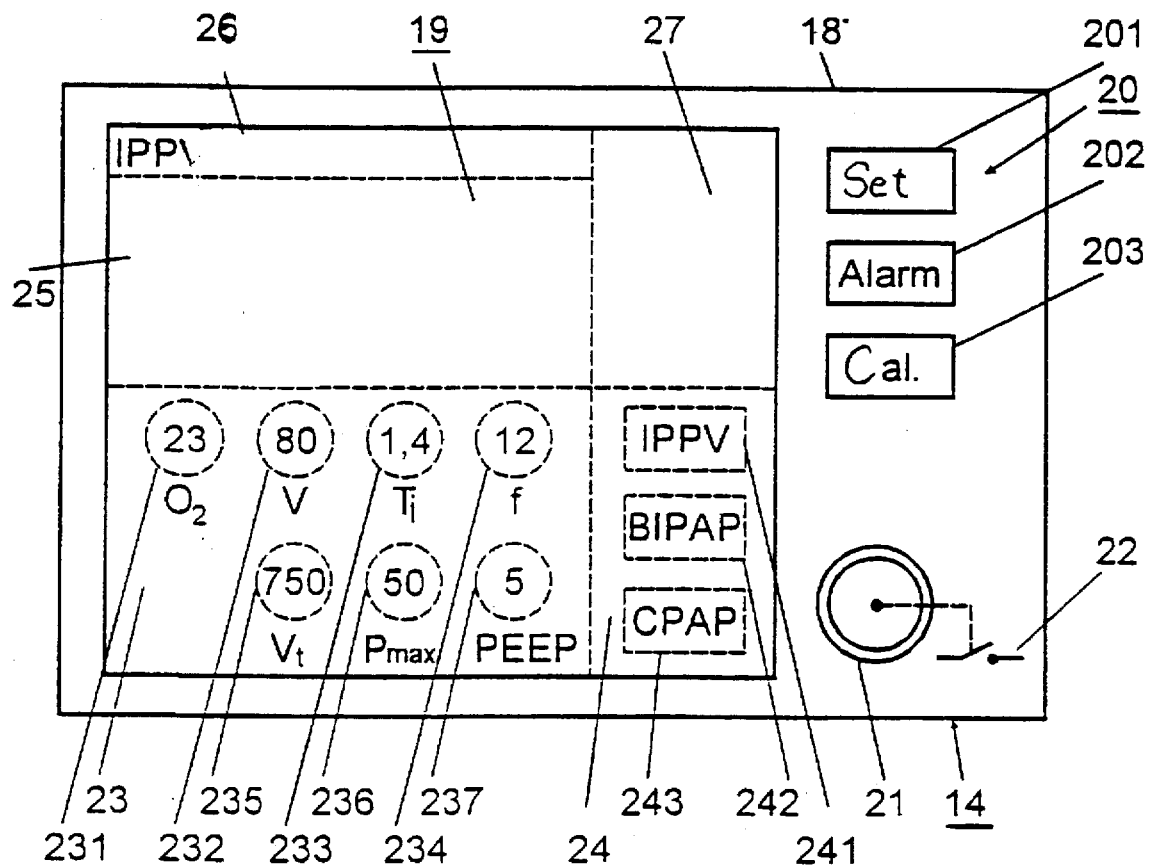
FIG. 2 is a top view of the operating unit.

FIG. 2 shows a top view of the operating unit 14. The operating unit 14 contains, in a housing 18, a flat screen 19 with a contact-sensitive surface, a keypad 20 with function keys for parameter setting 201, alarm setting 202, calibration 203, and a rotary knob 21 as the input element, with an acknowledge switch 22, which is actuated by depressing the rotary knob 21. The acknowledge switch 22 is arranged physically within the housing 18 and is schematically illustrated by a switch symbol on the front side of the operating unit 14 for greater clarity. The flat screen 19 is divided into a first data entry sector 23 with respiration parameter-setting segments 231, 232, 233, 234, 235, 236, 237 for the oxygen concentration $O_2$, the respiration gas flow V, the inspiration time $T_i$, the respiration rate f, the respiration stroke volume $V_r$, the maximum inspiration pressure Pmax, and the PEEP pressure, respectively, and a second data entry sector 24 with form of respiration-setting segments 241, 242, 243, and a first output sector 25, a second output sector 26, and a third output sector 27. The form of respiration-setting segments for the forms of respiration IPPV 241, BIPAP 242 and CPAP 243 are provided in the second input sector 24. Values which are variable in time, e.g., the respiration pressure or the respiration flow, are represented in the first output sector 25. The selected form of respiration, in this case "IPPV," is displayed in the second output sector 26. and the third output sector 27 is used to display measured values of, e.g., the respiratory minute volume and the inspiratory oxygen concentration.

A new form of respiration is set as follows. By depressing the function key for parameter setting 201, the segments 23, 24, 25, 26, 27 shown in FIG. 2 are activated on the flat screen 19 with respiration parameter-setting segments of the mode of respiration last selected, which are not shown in FIG. 2, and with the second data entry sector 24, which contains the form of respiration-setting segments 241, 242, 243. To set a new form of respiration, IPPV, the segment 241 is touched with the finger, and the parameter-setting segments 231, 232, 233, 234, 235, 236, 237 belonging to this form of respiration appear within the first data entry sector 23. The values of parameters currently set and of suggested values derived from the body weight are displayed within the respiration parameter-setting segments 231, 232, 233, 234, 235, 236, 237, and these values can be changed if necessary. If, e.g., the respiration stroke volume $V_r$ is to be changed, the parameter-setting segment 235 is touched. Upon touching the parameter-setting segment 235, the rotary knob 21 is switched into functional connection with the setting segment 235, and the parameter can then be increased by turning the rotary knob 21 to the right or decreased by turning the knob to the left. The acknowledge switch 22 is actuated by depressing the rotary knob 21, and the changed respiration stroke volume is now taken over as a new set value into the control unit 8. The selection of the form of respiration IPPV is confirmed by actuating the acknowledge switch 22 again. If no respiration parameter was changed before, the form of respiration IPPV selected is confirmed by depressing the rotary knob 21 once, i.e., by actuating the acknowledge switch 22. The new form of respiration IPPV just taken over is displayed in the second output sector 26.

The assignment of defined respiration parameter-setting segments 231, 232, 233, 234, 235, 236, 237 to a form of respiration setting segment 241 advantageously ensures that in a Special form of respiration, only the set parameters which are relevant for this form of respiration and can be changed are displayed. The clarity of the operating surface is improved as a result.

While a specific embodiment of the invention has been shown and described in detail to illustrate the application of the principles of the invention, it will be understood that the invention may be embodied otherwise without departing from such principles.

What is claimed is:

1. A respirator, comprising:

a gas-metering device for respiration gases;

control unit means for controlling and monitoring metering of respiration gases;

an input unit, connected to the said control unit means for introducing commands into said control unit means, said input unit including a keypad and an input element;

acknowledge switch means for input of changed parameter as a new set value for said control unit; and said input unit further comprising parameters display and input means for displaying parameters and changing preselected parameters, said parameters display and input means including an interactive flat screen with a contact-sensitive surface with data entry sectors having setting segments and with output sectors for parameters to be displayed, said data entry sectors including preselected data entry sectors which are switched into an active state on said flat screen by said keypad, said setting segments within said preselected data entry sector being actuatable in said active state and including means for switching one of said input element and said acknowledge switch means into functional connection with said selected setting segment upon actuation.

2. A respirator according to claim 1, wherein said keypad is arranged outside of said flat screen.

3. A respirator according to claim 1, wherein said keypad is arranged within said flat screen.

4. A respirator according to claim 1, wherein said display and input means including said flat screen, said keypad and said acknowledge switch are integrated in a modular operating unit, said gas metering device and said control unit being provided as respirator components, said modular operating unit being pivotable in relation to said respirator components.

5. A respirator according to claim 1, wherein said display end input means including said flat screen, said keypad and said acknowledge switch are integrated in a modular operating unit, said gas-metering device and said control unit being provided as respirator components, said operating unit being provided as a component that is detachable from said respirator components.

6. A respirator according to claim 1, wherein said flat screen is designed as a color screen.

7. A respirator according to claim 1, wherein said preselected data entry sectors include a first data entry sector with respiration parameter-setting segments and a second data entry sector with form of a respiration-setting segments, said actuation means of said form of respiration-setting segment being touch responsive for displaying respiration parameter-setting segments corresponding with the actuated form of respiration-setting segment.

8. A respirator according to claim 7, wherein said respiration parameter-setting segments are represented as setting knobs on said flat screen.

9. A respirator according to claim 7, wherein said form of respiration-setting segments are represented as keys on the said flat screen.

10. A respirator according to claim 7, wherein a set value of a parameter is displayed within said respiration parameter-setting segments.

11. A respirator according to claim 10, wherein said respirator parameter-setting segments include parameter displays, and further comprising means for deriving numerical values forming said parameter displays as suggested values based on body weight of a patient connected to the respirator.

* * * * *